United States Patent [19]

Panzer

[11] Patent Number: 4,672,954

[45] Date of Patent: Jun. 16, 1987

[54] SEXUAL AID

[76] Inventor: Jack S. Panzer, 12930 Denmark, Detroit, Mich. 48217

[21] Appl. No.: 783,473

[22] Filed: Oct. 3, 1985

[51] Int. Cl.$^4$ ............................................... A61F 5/41
[52] U.S. Cl. ....................................................... 128/79
[58] Field of Search .......................................... 128/79

[56] References Cited

U.S. PATENT DOCUMENTS

| 853,410 | 5/1907 | Huebner | 128/79 |
| 1,144,083 | 3/1969 | Rydlewski | 128/79 |
| 3,920,007 | 11/1975 | Line | 128/79 |
| 4,362,152 | 12/1982 | Gorokhovsky et al. | 128/79 |
| 4,449,521 | 5/1984 | Panzer | 128/79 |

FOREIGN PATENT DOCUMENTS

| 183924 | 4/1906 | Fed. Rep. of Germany | 128/79 |
| 142022 | 1/1935 | Fed. Rep. of Germany | 128/79 |
| 547535 | 9/1942 | United Kingdom | 128/79 |
| 884357 | 12/1961 | United Kingdom | 128/79 |
| 1144083 | 3/1969 | United Kingdom | 128/79 |

Primary Examiner—John J. Wilson
Assistant Examiner—Cary E. Stone
Attorney, Agent, or Firm—Gifford, Groh, VanOphem, Sheridan, Sprinkle and Dolgorukov

[57] ABSTRACT

A genital splint for permitting a human male to achieve penetration during sexual intercourse is easily sized to individual penile diameters, yet is both positively secured and readily removable from the penis. The splint includes a pair of rigid but slightly flexible rods adjacently contained in a somewhat elastic encasement. Pairs of arcuate members are affixed to the ends of the rods so as to form a base ring closely fitting about the root of the penis, and a collar closely fitting about the corona of the penis. The collar is closed by an elastomeric member fitting over the free ends of the coronal arcuate members. The free ends of the collar members pivot away from one another upon movement of the base members away from one another, either to allow sizing of the splint to different penile diameters, or prevent any discomforting tightness upon partial or full erection of the penis.

10 Claims, 6 Drawing Figures

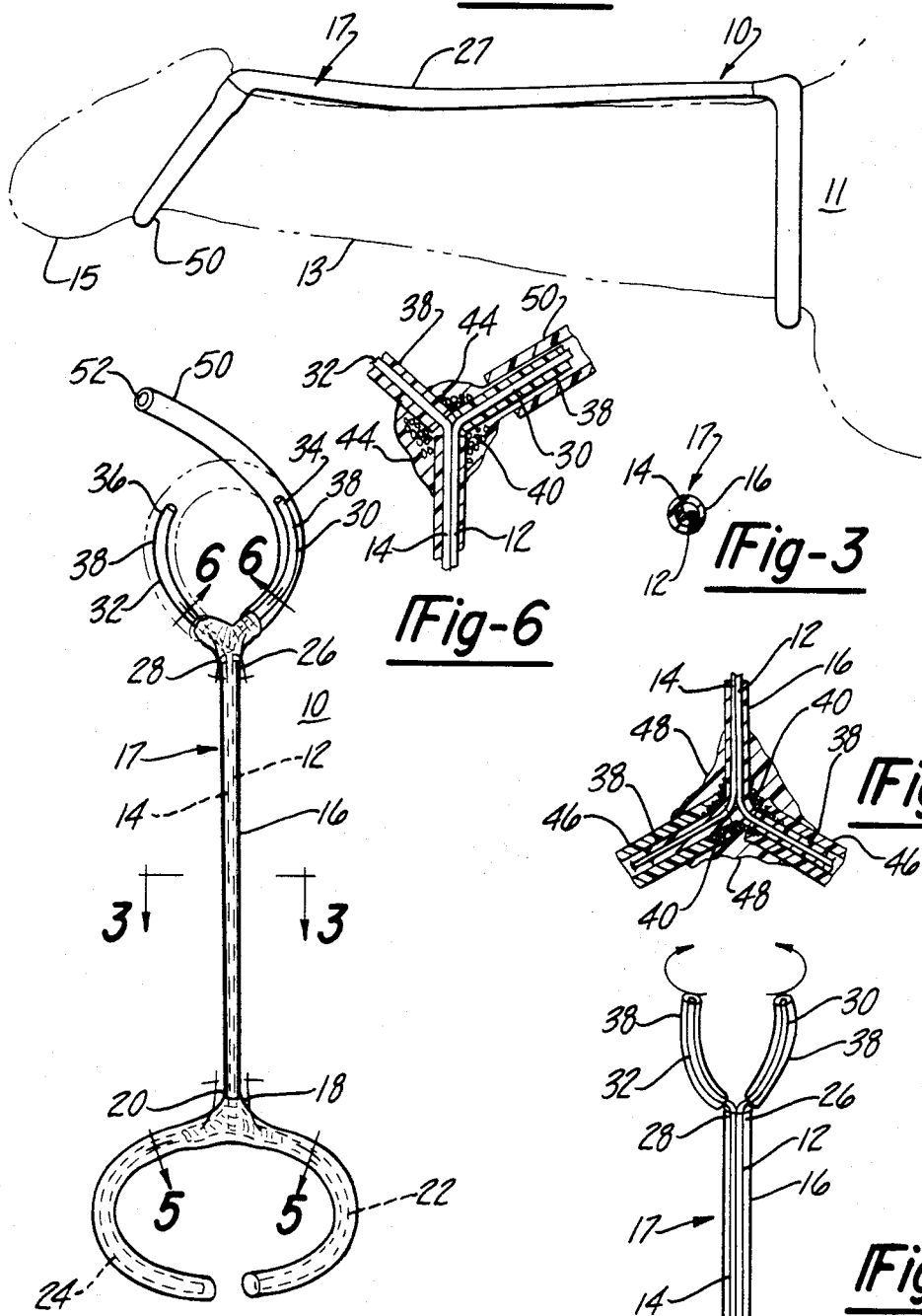

SEXUAL AID

BACKGROUND OF THE INVENTION

I. Field of the Invention

The present invention relates generally to medical applicances, and more particularly, to a genital splint to permit a male to achieve penetration during sexual intercourse.

II. Description of the Prior Art

Normal male-female sexual relations are often hindered by the failure of the male to obtain or maintain a satisfactory erection of the penis. Without regard whether the problem is psychological or physiological, penetration may be impossible unless some form of sexual aid is used. One convenient type of sexual aid comprises a splint-type structure, which stretches the penis and supports it outwardly from the body.

One such previously known device is described in U.S. Pat. No. 3,920,007, to Line, owned by the Applicant herein. The sexual aid disclosed by Line includes a ring-like base which slidably receives the penis therethrough. A rigid support column extends perpendicularly to the ring-like base and includes a collar adapted for engagement with the corona of the glans of the penis, whereby the penis is supported in an extended position outwardly from the body, the collar compressingly engaging the glans.

Another such device is disclosed in Applicant's U.S. Pat. No. 4,449,521. The sexual aid disclosed therein includes a split-ring base, an elongated and adjustable support column extending perpendicularly from the base, an adjustable collar compressingly engaging the glans of the penis, and a pliable coating covering each of these elements. The support column is surrounded by an elasitcally extendable means which is engageable with the base ring so as to fix the length of the support column. The split-ring base permits the base to engage and expand with the penis throughout various stages of erection. Additionally, the collar is formed so that no relatively sharp ends of the collar can become exposed when a glans supporting tube becomes displaced from the collar; rather, upon such displacement, only a pliant coating is exposed.

A third such device is disclosed in U.S. Pat. No. 4,362,152, issued to Gorokhovsky et al. The device disclosed therein includes a pair of substantially rigid rods disposed side by side in a common elastic encasement. The rods are dorsally secured about the scrotum at the root of the penis by a loop of elastomeric tubing. A yoke is attached to the ends of the rods opposite the tube, encircling the glans of the penis around and in abutment with the corona. The ends of the yoke arms remain in abutting contact upon erective expansion of the glans, while such expansion causes the arms of the yoke to rotate relatively further apart and cause the elastomeric securing tube to stretch, and exert increasing pressure on the dorsal vein.

The use of the Gorokhovsky et al device in particular has been subject to several drawbacks. A large number of measurements (generally six or seven) have been necessary in order to size the device to a particular patient. Moreover, the yoke assembly does not ensure a positive securement of the device to the penis. The device does not remain comfortably fitting upon erection of the penis, since upon erection the yoke arms rotate relatively away from each other, causing the rods to exert increasing pressure on the dorsal vein and corpora cavernosa, while erection makes such pressure undesireable.

SUMMARY OF THE PRESENT INVENTION

The present invention provides a device which is easily sized to individual penile diameters, and which remains comfortably fitting upon erection of the penis. The device also ensures the positive securement of the device to the penis, yet which remains easily releasable upon erection. The sexual aid according to the present invention comprises a parallel pair of somewhat rigid but slightly flexible adjacent rods encased in a slightly elastic encasement, so that the rods are rotatable against one another. Each of the rods has one end disposable adjacent the root of the penis, and another end disposable adjacent the corona of the penis. The rods extend alongside the dorsal side of the penis, and possess a slight upward bend about two-thirds of the way from their root ends to their coronal ends, so as to apply pressure to the dorsal vein of the penis.

The sexual aid of the present invention also comprises a pair of arcuate base members affixed one each to the root ends of the rods, disposed about perpendicularly to the rods. Together the base members form a base ring abuttable against the torso, disposed closely about and substantially encircling the root of the penis. Because of the encasement of the rods, their base members are pivotable relative to one another. Such pivoting can occur either upon erection of the penis, or by the manual adjustment of the device to fit a penis of a particular diameter.

The sexual aid further includes a pair of arcuate collar members affixed one each to the coronal ends of the rods, each of the collar members possessing a free end. The free ends of the collar members are urged away from one another upon the pivoting of the base members away from each other.

Lastly, the sexual aid includes an elastomeric tube fitted over the free ends of the collar members, so as to form a collar about the corona of the penis. The collar is angled about 45 degrees relative to the rods. Preferably, the rods and base and collar members are constructed from 0.032 inch piano spring wire, so that the sexual aid is rigid, but deformable to match the size of a particular penis. Movement of the base members away from one another somewhat increases the diameter of the collar, avoiding the danger of increasing pressure on the penis during erection.

BRIEF DESCRIPTION OF THE DRAWING

The present invention will be better understood by reference to the following detailed description, when read in conjunction with the accompanying drawing, wherein like reference characters refer to like parts throughout the several views, and in which:

FIG. 1 is a side plan view of the preferred embodiment of the present invention;

FIG. 2 is a perspective view of the preferred embodiment of the present invention;

FIG. 3 is a cross-sectional view taken along line 3—3 of FIG. 2;

FIG. 4 is a perspective view similar to FIG. 2, with parts removed for clarity;

FIG. 5 is a cross-sectional view taken along line 5—5 of FIG. 2; and

FIG. 6 is a cross-sectional view taken along line 6—6 of FIG. 2.

DETAILED DESCRIPTION OF THE PREFERRED EMBODIMENT OF THE PRESENT INVENTION

With reference first to FIGS. 2 through 4, a sexual aid 10 in accordance with the present invention is thereshown and includes a column 17 comprising a parallel pair of somewhat rigid but slightly flexible adjacent rods 12 and 14 encased in a slightly elastic casement 16. Preferably, the rods 12 and 14 are constructed from 0.032 inch piano spring wire. The rods 12 and 14 are contained in the casement 16 such that the rods are rotatable against one another.

The rods 12 and 14 each have a first end 18 or 20, respectively, disposable adjacent the root 11 of a penis 13 (FIG. 1). A pair of arcuate base members 22 and 24 are one each perpendicularly affixed to, and preferably intergrally formed with, the root ends 18 and 20 of the rods 12 and 14.

The rods 12 and 14 also comprise a second end 26 or 28, respectively, disposable adjacent the corona 15 of the penis 13, such that the rods 12 and 14 extend alongside the dorsal surface of the penis 13. Each of the rods 12 and 14 possess a slight upward bend 27 of about 10 degrees, about two-thirds of the way from the root ends 18 and 20 to the coronal ends 26 and 28, to facilitate the application of pressure to the dorsal vein of the penis 13. A pair of arcuate collar members 30 and 32 are affixed to and preferably integrally formed with the coronal ends 26 and 28 of the rods 12 and 14. The collar members 30 and 32 are dimensioned such that they extend only part-way around the corona 15 of the penis 13. Each of the members 30 and 32 possess a free end 34 or 36, respectively. The collar members 30 and 32 are disposed at an angle of about 45 degrees relative to the rods 12 and 14.

The casement 16 is preferably constructed from a durable synthetic material, such as silicon or teflon tubing or the like, possessing sufficient elasticity such that the rods 12 and 14 are rotatable against one another. The base members 22 and 24 are thus pivotable relative to one another, and the pivoting of the base members 22 and 24 away from each other urges the free ends 34 and 36 of the collar members 30 and 32 away from one another. The base members 22 and 24 and the collar members 30 and 32 are covered with a durable coating 38 (FIGS. 5 and 6), preferably constructed from the same material as the casement 16.

In order to maintain the rods 12 and 14 and their affixed members in longitudinal alignment, and to control the resistance of the rods to rotation against one another (and thereby control the pivoting of the base members 22 and 24, and the collar members 30 and 32), the root ends 18 and 20 and the coronal ends 26 and 28 of the rods 12 and 14 are wrapped with threading 40. This threading 40 is external to the durable coating 38 and the casement 16. The threading 40 also wraps about the proximal portions of the base members 22 and 24, and the collar members 30 and 32. A resilient coating 44 is disposed atop the coronal threading to prevent the separation or unraveling thereof. The rotation of the rods 12 and 14 tends to slightly straighten the column 17, because their alignment is maintained. This serves to ease the pressure applied to the dorsal vein by the bend 27, increasing the comfort of the user when an erection is achieved.

A flexible coating 46 is disposed over the root end threading 40 and the durable coating 38 on the base members 22 and 24. This flexible coating preferably comprises silicon tubing disposed on the base members 22 and 24. At the joint with the root ends 18 and 20 of the rods 12 and 14, the flexible coating 46, the root threading 40 and the root ends 18 and 20 are all covered with a resilient coating 48, like the coronal resilient coating 44. The coatings 44 and 48 preferably comprise a resilient and highly flexible silicon elastomer.

A collar is formed about the corona 15 by an elastic means extending between the free ends 34 and 36 of the collar members 30 and 32. Preferably, the elastic means comprises an elastomeric silicon tube 50 fitting over the free ends 34 and 36 of the collar members 30 and 32. Advantageously, the friction between the tube 50 and the durable coating 38 on the collar members 30 and 32 is sufficient to keep the tube 50 on the collar members 30 and 32 during the time that the collar is engaged about the corona 15, but which still allows the tube 50 to be easily manually slid along and removed from the collar members 30 or 32. Preferably, one end 52 of the elastomeric tube is slid along the full length of one of the collar members, such as collar member 30, and anchored in place over the resilient coronal coating 44. Advantageously, the resilient coating 44 is sufficiently adhesive prior to curing so as to allow the permanent affixment of the end 52 of the tube 50 over the collar member 30 by embedment therein. The free end 52 of the tube 50 is still free to be slid along the other collar member 32.

The base members 22 and 24 and the collar members 30 and 32 are sufficiently deformable so as to enable the device to be matched to the diameter of the root 11 and the corona 15 of the penis 13. The friction between the rods 12 and 14 is preferably of one of two degrees. A first degree of friction is sufficiently strong that the rotation of the rods 12 and 14 relative to one another is accomplished only by the manual manipulation of the base members 22 and 24, and/or the collar members 30 and 32, so as to size the sexual aid 10 to the patient. A second, preferred degree of friction is less than this first degree of friction, and is such that the relative rotation of the rods 12 and 14 may be had upon erection of the penis, so as to move the free ends 34 and 36 of the collar members 30 and 32 apart, thereby expanding the collar upon expansion of the penis.

Use of the sexual aid 10 as a genital splint is straightforward. The free end 52 of the elastomeric tube 50 is disengaged from the collar member 32. The penis 13 is then inserted through the base ring formed by the base members 22 and 24 towards the collar until the corona 15 of the glans engages the collar, such that the base members 22 and 24 abut the torso, and are disposed closely about and substantially encircling the root 11 of the penis 13. The free end 52 of the elastomeric tube 50 is slid over the free end 36 of the collar member 32 and slid sufficiently thereon until a comfortable fit of the collar about the corona 15 is obtained.

If the sexual aid 10 is constructed such that the second, lesser degree of friction exists between the rods 12 and 14, partial or complete erection of the penis will result in the movement of the base members 22 and 24 away from each other, so that the free ends 34 and 36 of the collar members 30 and 32 move away from one another. Because the tube 50 is elastic, this results in an expansion of the size of the collar commensurate with the degree of erection, maintaining the comfort of the patient. The sexual aid 10 thus remains in place on the patient throughout erection, and in particular, positive securement of the collar about the corona 15 is ensured. Either during or after use, if it is desired to remove the sexual aid 10 from the penis 13, the elastomeric tube 50 is removed from the collar member 32 and the device withdrawn, the base members 22 and 24 and the collar members 30 and 32 being manually spread apart if necessary.

Alternatively, if the first degree of friction is provided between the rods 12 and 14, pivoting of the base members 22 and 24 during erection is not expected to occur. Instead, such pivoting is manually brought about in order to size the sexual aid 10 to the particular patient. The flexibility or the formability of the wire comprising the rods and members allows the aid 10 to be fit to any penis, without requiring significant measurement other than the length from the root to the corona. The diameter of the base and collar can be set independently of one another. This adjustment can be done by either the doctor or the patient himself without the need of any tools, or special expertise or training. This makes the device easier for the patient to use properly than have been other known devices. The elimination of numerous diametrical measurements also makes it less expensive to provide the device to a patient.

Having thus described my invention, however, many modifications thereto will become apparent to those skilled in the art to which it pertains, without deviation from the spirit of the present invention, as defined by the scope of the appended claims.

I claim:

1. A sexual aid for use by a human male comprising:
   a parallel pair of somewhat rigid but slightly flexible rods adjacently encased in a slightly elastic casement, so that said rods are rotatable against one another, each of said rods having one end disposable adjacent the root of the penis, and another end disposable adjacent the corona of the penis, and forming a column disposable alongside the dorsal surface of the penis;
   an arcuate base member affixed to said root end of each of said rods, disposed about perpendicularly thereto, such that said base members together form a base ring abuttable against the torso, disposable closely about and substantially encircling the root of the penis, so that said base members are pivotable relative to one another;
   an arcuate collar member affixed to said coronal end of each of said rods, each collar member possessing a free end, such that said free ends are urged away from one another upon pivoting of said base members away from each other; and
   elastic means extending between such free ends of said collar members for forming, in combination with said collar members, a collar about the corona of the penis.

2. The invention according to claim 1, wherein said rods comprise about 0.032 inch piano spring wire.

3. The invention according to claim 1, wherein said base members pivot away from one another upon erection of the penis, so that said collar extends upon such erection.

4. The invention according to claim 1, wherein said elastic means comprises a silicon tube disposed over said arcuate collar members.

5. The invention according to claim 1, wherein said casement comprises a synthetic material.

6. The invention according to claim 1, wherein said base members and said collar members are deformable independently of one another to match the root and coronal diameter of the penis.

7. The invention according to claim 1, wherein each of said rods possesses a slight upward bend about two-thirds of the way from said root end to said coronal end, so as to facilitate the application of pressure to the dorsal vein of the penis.

8. The invention according to claim 7, wherein said upward bend is about 10 degrees.

9. The invention according to claim 1, wherein said collar is bent about 45 degrees downwardly from said rods.

10. The invention according to claim 1, wherein said base members are manually pivotable away from one another in order to size said aid to the penis.

* * * * *